United States Patent

Lehmann

(10) Patent No.: US 6,184,005 B1
(45) Date of Patent: Feb. 6, 2001

(54) ENZYMATIC RESOLVATION FOR OBTAINING A (−)-3,4-TRANS-DIARYLCHROMAN

(75) Inventor: Søren Lehmann, Frederiksberg (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/298,089

(22) Filed: Apr. 22, 1999

Related U.S. Application Data

(60) Provisional application No. 60/084,585, filed on May 7, 1998.

(30) Foreign Application Priority Data

Apr. 28, 1998 (DK) .................................................... 0579/98

(51) Int. Cl.$^7$ ............................... C12P 17/18; C12P 17/06
(52) U.S. Cl. ............................ 435/119; 435/125; 435/280
(58) Field of Search .................................... 435/119, 125, 435/280

(56) References Cited

U.S. PATENT DOCUMENTS

| 4,447,622 | 5/1984 | Salman et al. | 348/528 |
| 5,089,637 | 2/1992 | Urban | 549/407 |

OTHER PUBLICATIONS

Chemical Abstract of Japan No. J07067690 Mar. 14, 1995.
Chemical Abstract of Japan No. J08084598 Apr. 2, 1996.

*Primary Examiner*—Herbert J. Lilling
(74) *Attorney, Agent, or Firm*—Steve T. Zelson; Valeta Gregg

(57) ABSTRACT

The invention relates to a process for the preparation of (−)-3,4-trans-compounds involving an enzymatic hydrolysis. These compounds and their salts are useful in the treatment of bone loss, hyperlipoproteinaemia, hypertriglyceridaemia, hyperlipidaemia, or hypercholesterolaemia or arteriosclerosis or in anticoagulative treatment.

20 Claims, No Drawings

ENZYMATIC RESOLVATION FOR OBTAINING A (−)-3,4-TRANS-DIARYLCHROMAN

CROSS-REFERENCE TO RELATED APPLICATIONS

This application is a claims priority under 35 U.S.C. 119 of Danish application serial no. PA 1998 00579 filed Apr. 28, 1998 and U.S. application Ser. No. 60/084,585 filed May 7, 1998, the contents of which are fully incorporated herein by reference.

FIELD OF INVENTION

The present invention relates to a new process for the preparation of (−)-3,4-trans-compounds involving an enzymatic hydrolysis.

BACKGROUND OF THE INVENTION

U.S. Pat. No. 5,280,040 discloses a class of 3,4-diarylchromans and their salts useful in the treatment of bone loss. Furthermore, PCT/DK96/00014 discloses that these compounds are useful in the treatment of hyperlipoproteinaemia, hypertriglyceridaemia, hyperlipidaemia, or hypercholesterolaemia or arteriosclerosis or for anticoagulative treatment. PCT/DK96/00015 discloses that these compounds are useful in the treatment of gynaecological disorders, such as endometriosis, dysfunctional bleedings, endometrial cancer, polycystic ovarian syndrome and anovulatoric bleeding and for the induction of endometrial thinning. The compounds are also known to have useful effects on gynaecomastia, obesity, vasodilation (respectively from PCT/DK96/00012, PCT/DK96/00011, and PCT/DK96/00013) and furthermore on e.g. Alzheimers disease (PCT/DK96/00010).

A process for the preparation of (+,−)-3,4-trans diarylchromanes is described in U.S. Pat. No. 3,822,287 and by Suprabhat Ray et al. in J.Med.Chem.19,276 (1976). The (+,−)-3,4-trans-isomer is obtained by conversion of the (+,−)-3,4-cis-isomer by means of an organometallic base-catalyzed rearrangement as described in U.S. Pat. No. 3,822,287.

The resolvation of (+,−)-3,4-trans-7-methoxy-2,2-dimethyl-3-phenyl-4-{4-[2-(pyrrolidin-1-yl)ethoxy]phenyl}chromane in its optical antipodes is described in U.S. Pat. No. 4,447,622. According to this process the (+,−)-3,4-trans-7-methoxy-2,2-dimethyl-3-phenyl-4-{4-[2-(pyrrolidin-1-yl)ethoxy]phenyl}chromane is reacted with di-p-toluoyl-l-tartaric acid monohydrate in a protic solvent, the reaction mixture is subjected to fractional crystallization and the crystalline salt is subjected to alkaline hydrolysis to produce the desired enantiomer.

Example 1 of U.S. Pat. No. 4,447,622 describes the preparation of the (−)-3,4-trans enantiomer, shown by the following formula:

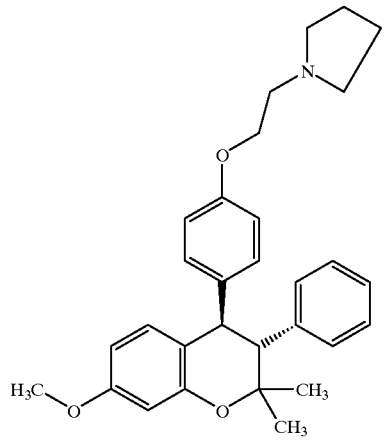

When using the process disclosed in U.S. Pat. No. 4,447,622 the desired (−)-3,4-trans enantiomer is only obtained with a low chiral purity, less than 80% ee (enantiomeric excess) after the first crystallization. In order to improve the chiral purity the enantiomer has to be crystallized several times.

One object of the present invention is therefore to provide a new process involving an enzymatic resolution step for the preparation of (−)-3,4-trans enantiomers of compounds of formula I which process is adaptable to large scale manufacture, provide good yields and high purity and reduce the cost of manufacture.

DESCRIPTION OF THIS INVENTION

The present invention concerns a process for the preparation of (−)-3,4-trans-compounds of the formula I

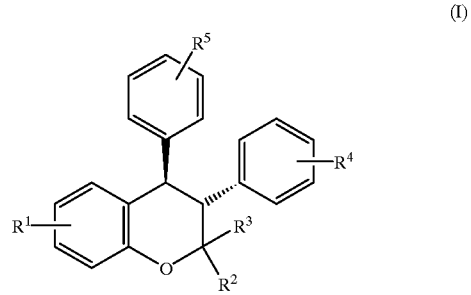

(I)

wherein $R^1$ and $R^4$ are individually hydrogen, $C_{1-6}$alkyl or $C_{1-6}$alkoxy, $R^5$ is —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6-membered heterocyclic group containing one or two heteroatom(s) which heterocyclic group is optionally substituted with $C_{1-6}$alkyl; and $R^2$ and $R^3$ are individually hydrogen or $C_{1-6}$alkyl; or a salt thereof, which comprises a) treating a cis-racemate of a compound of formula V

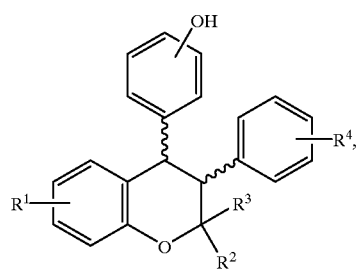

(V)

or a salt thereof, wherein $R^1$, $R^2$, $R^3$ and $R^4$ are as defined above with an agent of formula R—CO—X, wherein R is $C_{1-12}$alkyl, optionally substituted with $C_{1-6}$alkyl, $C_{1-6}$ alkoxy, hetaryl or aryl or $C_{1-12}$alkoxy, optionally substituted with $C_{1-6}$alkyl, $C_{1-6}$alkoxy, hetaryl or aryl, and X is a leaving group, thereby providing a cis-racemate of a compound of formula VI

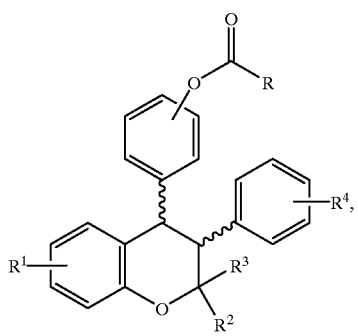

(VI)

or a salt thereof, wherein R, $R^1$, $R^2$, $R^3$ and $R^4$ are as defined above, b) treating said cis-racemate of formula VI with an enzyme having lipase activity, thereby providing a mixture comprising a compound of formula VIa

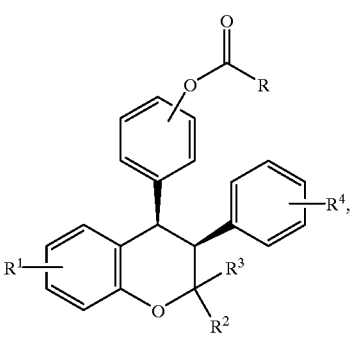

(VIa)

or a salt thereof, and a compound of formula VII

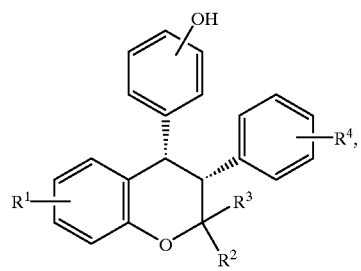

(VII)

or a salt thereof;

or a mixture comprising a compound of formula VIb

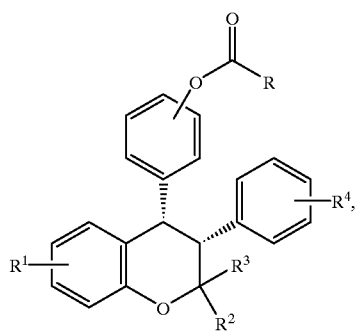

(VIb)

or a salt thereof, and a compound of formula VIIa

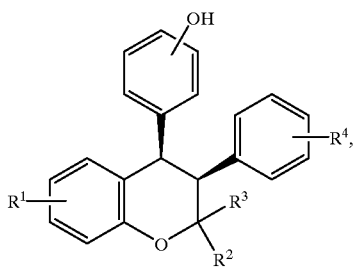

(VIIa)

or a salt thereof, c) separating said mixture of compound VIa and VII or said mixture of compound VIb and VIIa, thereby obtaining a compound of formula VII or a compound of formula VIb, which compound VIb is then hydrolyzed to said compound of formula VII, d) treating said compound of formula VII or a salt thereof, with an agent of formula Y-$R^5$ wherein Y is a leaving group, thereby providing a compound of formula VIII

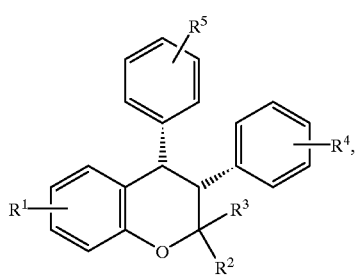

(VIII)

or a salt thereof, e) treating said compound of formula VIII or a salt thereof with a strong base in an aprotic solvent, thereby obtaining said compound of formula I or a salt thereof.

The above process may also be carried out by starting with a trans-racemate in step a), thus the process comprises a) treating a trans-racemate of a compound of formula II

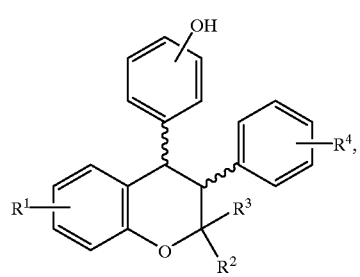

(II)

or a salt thereof, wherein $R^1$, $R^2$, $R^3$ and $R^4$ are as defined above with an agent of formula R—CO—X, wherein R is $C_{1-12}$alkyl, optionally substituted with $C_{1-6}$-alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby providing a trans-racemate of a compound of formula III

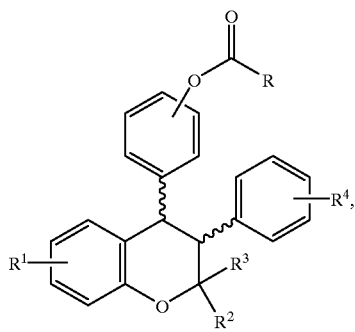

(III)

or a salt thereof, wherein $R^1$, $R^2$, $R^3$ and $R^4$ are as defined above, b) treating said trans-racemate of formula III with an enzyme having lipase activity, thereby providing a mixture comprising a compound of formula IIIa

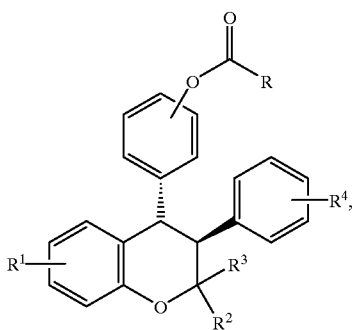

(IIIa)

or a salt thereof, and a compound of formula IV

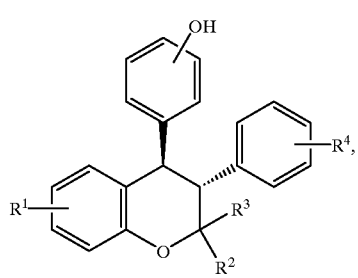

(IV)

or a salt thereof;
or a mixture comprising a compound of formula IIIb

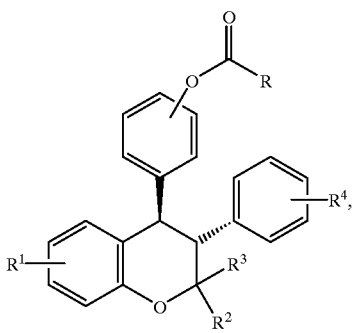

(IIIb)

or a salt thereof, and a compound of formula IVa (IVa)

or a salt thereof, c) separating said mixture of compound IIIa and IV or said mixture of compound IIIb and IVa, thereby obtaining a compound of formula IV or a compound of formula IIIb, which compound IIIb is then hydrolyzed to said compound of formula IV, d) treating said compound of formula IV with an agent of formula Y-R$^5$ wherein Y is a leaving group, thereby obtaining the compound of formula I or a salt thereof.

In another aspect the invention concerns a process for the preparation of (3R,4S)-cis-compounds of the formula VII (VII)

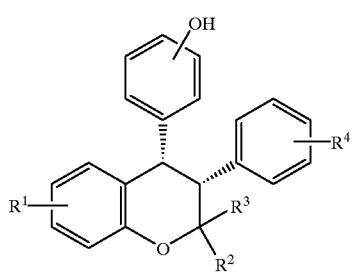

wherein R$^1$ and R$^4$ are individually hydrogen, C$_{1-6}$alkyl or C$_{1-6}$alkoxy, and R$^2$ and R$^3$ are individually hydrogen or C$_{1-6}$alkyl; or a salt thereof, which comprises a) treating a cis-racemate of formula VI (VI)

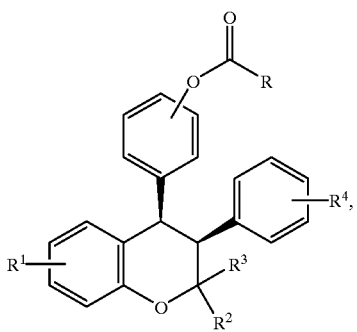

or a salt thereof, wherein R is C$_{1-12}$alkyl, optionally substituted with C$_{1-6}$alkyl, C$_{1-6}$alkoxy, hetaryl or aryl or C$_{1-12}$alkoxy, optionally substituted with C$_{1-6}$alkyl, C$_{1-6}$alkoxy, hetaryl or aryl, and R$^1$, R$^2$, R$^3$ and R$^4$ are as defined above, with an enzyme having lipase activity, thereby providing a mixture comprising a compound of formula VIa (VIa)

or a salt thereof, and a compound of formula VII (VII)

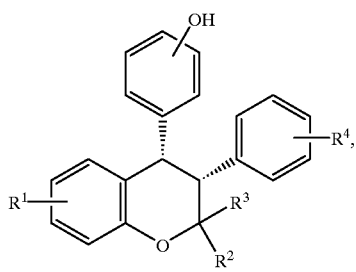

or a salt thereof or a mixture comprising a compound of formula VIb (VIb)

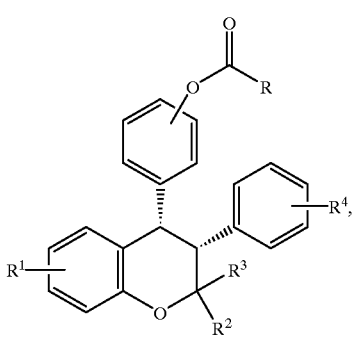

or a salt thereof, and a compound of formula VIIa (VIIa)

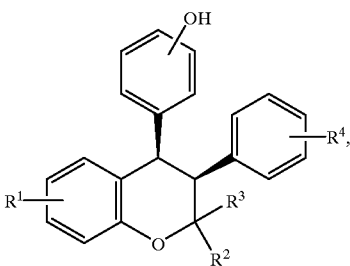

or a salt thereof, b) separating said mixture of compound VIa and VII or said mixture of compound VIb and VIIa, thereby obtaining a compound of formula VII or a compound of formula VIb, which compound VIb is then hydrolyzed to said compound of formula VII.

In a further aspect the invention concerns a process for the preparation of (3R,4R)-trans-compounds of the formula IV

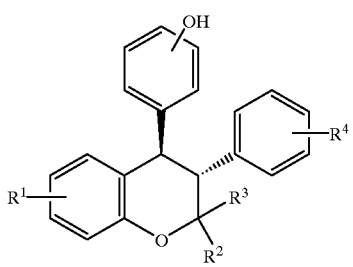

(IV)

wherein $R^1$ and $R^4$ are individually hydrogen, $C_{1-6}$alkyl or $C_{1-6}$alkoxy, and $R^2$ and $R^3$ are individually hydrogen or $C_{1-6}$alkyl; or a salt thereof, which comprises a) treating a trans-racemate of formula III

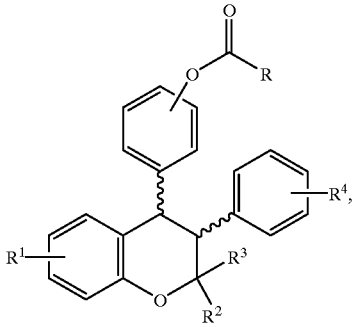

(III)

or a salt thereof, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and $R^1$, $R^2$ $R^3$ and $R^4$ are as defined above, with an enzyme having lipase activity, thereby providing a mixture comprising a compound of formula IIIa

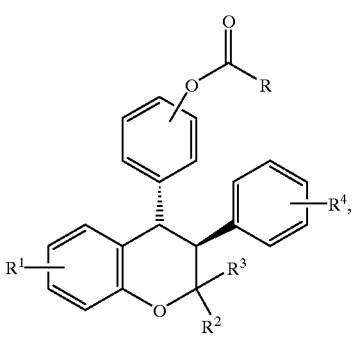

(IIIa)

or a salt thereof, and a compound of formula IV

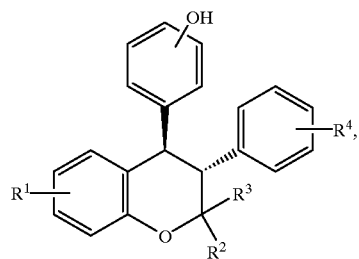

(IV)

or a salt thereof;
or a mixture comprising a compound of formula IIIb

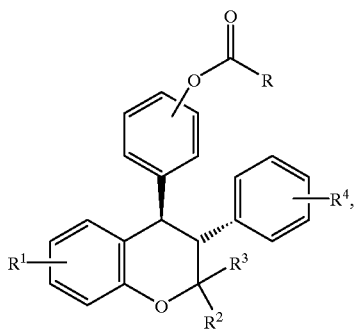

(IIIb)

or a salt thereof, and a compound of formula IVa

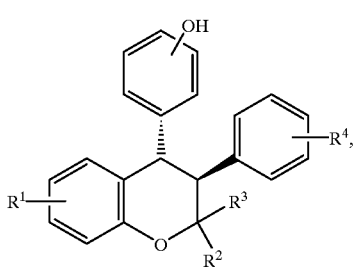

(IVa)

or a salt thereof,
b) separating said mixture of compound IIIa and IV or said mixture of compound Ib and IVa, thereby obtaining a compound of formula IV or a compound of formula IIIb, which compound IIIb is then hydrolyzed to said compound of formula IV, or a salt thereof.

Preferred compounds of formula I are those in which $R^1$ is $C_{1-6}$alkoxy, especially methoxy. Furthermore, $R^2$ and $R^3$ preferably are the same and $C_{1-6}$alkyl, especially methyl; $R^4$ is preferably hydrogen; and $R^5$ is preferably —O—$(CH_2)_n$—$NR^6R^7$ wherein n is 2 and $R^6$ and $R^7$ together with the N atom is a saturated or unsaturated 5- or 6-membered heterocyclic group containing one or two heteroatom(s) and optionally substituted with $C_{1-6}$alkyl. Within particularly preferred embodiments, $R^1$ is in the 7-position and is $C_{1-6}$alkoxy, particularly methoxy; each of $R^2$ and $R^3$ is methyl, $R^4$ is hydrogen, and $R^5$ is in the 4-position and is 2-(pyrrolidin-1-yl)ethoxy.

Preferred compounds of formula IV and VII are those in which $R^1$ is $C_{1-6}$alkoxy, especially methoxy. Furthermore, $R^2$ and $R^3$ preferably are the same and $C_{1-6}$alkyl, especially methyl; $R^4$ is preferably hydrogen. Within particularly preferred embodiments, $R^1$ is in the 7-position and is $C_{1-6}$alkoxy, particularly methoxy; each of $R^2$ and $R^3$ is methyl, $R^4$ is hydrogen, and the hydroxy group is in the 4-position.

A preferred embodiment of the invention provides a process for the preparation of (−)-3R,4R-trans-7-methoxy-2,2-dimethyl-3-phenyl-4-{4-[2-(pyrrolidin-1-yl)ethoxy]phenyl}chromane, herein referred to as levormeloxifene, or a salt thereof prepared from 3,4-cis-(+/−)-4-hydroxyphenyl-7-methoxy-2,2-dimethyl-3-phenylchromane or a salt thereof.

In one embodiment of the above process according to the invention in the agent of formula R—CO—X, R is $C_{1-12}$alkyl or $C_{1-12}$alkoxy. In a particular embodiment R is $C_{1-12}$alkyl, such as $C_{1-6}$alkyl, e.g. methyl, ethyl or pentyl. In another embodiment X is a halogen or a group of formula —O—CO—$C_{1-6}$alkyl, such as chloro or —O—CO—$CH_3$.

In another embodiment of the present process the enzyme is a lipase. In particular suitable lipases are candida antartica lipase B, Lipozyme, Humicola, *Pseudomonas cepasia, Candida cylindracea*, Pig liver esterase and Pig pancreas lipase.

In a further embodiment of the present process in the agent of formula Y—$R^5$, Y is a halogen, such as chloro.

In a still further embodiment of the present process the strong base in an aprotic solvent is potassium hydroxide in dimethylsulfoxide and toluene, or potassium t-butoxide in N-methylpyrrolidine and toluene.

The stereoselective rearrangement of the (−)-3,4-cis enantiomer of formula VIII to the corresponding (−)-3,4-trans enatiomer of formula I is possible without any loss of chiral purity.

By the process disclosed in U.S. Pat. No. 4,447,622 the (−)-3,4-trans enantiomer is only obtained in a chiral purity above 80% ee (enantiomeric excess) by crystallization several times.

The process of the invention is illustrated in the following schemes 1 and 2, wherein the synthesis of levormeloxifene (5) involves an enzymatic resolution step which overcomes a number of problems associated with a purely chemical resolution step.

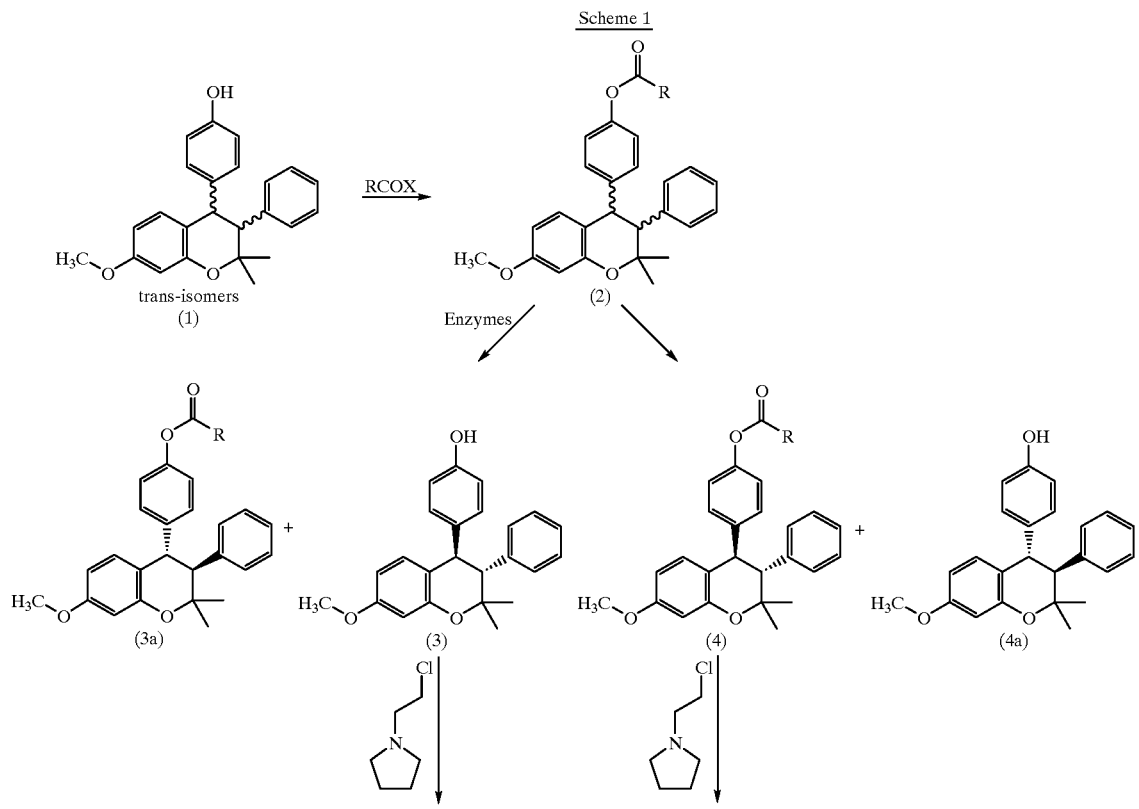

Scheme 1

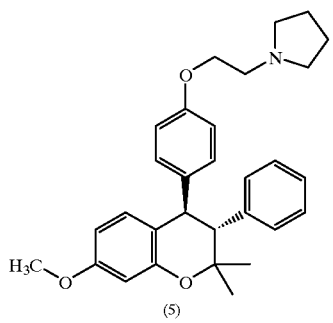
(5)

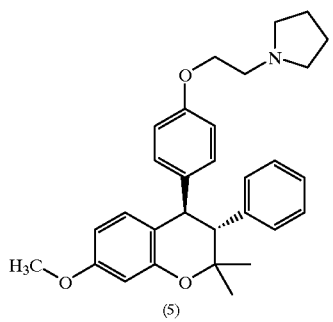
(5)

Trans-racemate of formula (1) is treated with an acylating agent, such as an agent of formula R—CO—X, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby obtaining the protected trans-racemate of formula (2). The trans-isomers of formula (1) are commercially available or may be prepared according to well defined procedures disclosed in the prior art starting from commercially available starting compounds. Moreover, trans-isomers of formula (1) may be prepared from the corresponding cis-isomers (6), illustrated in scheme 2 below, by treating the cis-isomers (6) with a base in an organic solvent, e.g. potassium hydroxide in toluene and dimethylsulfoxide, and working up in a suitable manner, e.g. by treatment with hydrochloric acid and filtering off the product, thereby obtaining the trans-isomers of formula (1). The trans-isomers of formula (2) are then treated with an enzyme having lipase activity, e.g. candida antartica lipase B, Lipozyme, Humicola, *Pseudomonas cepasia*, *Candida cylindracea*, Pig liver esterase and Pig pancreas lipase, in a suitable solvent, such as an organic solvent, e.g. n-hexane, n-heptane, acetonitril, methanol or ethanol, or an aqueous/organic solvent mixture, e.g. water/n-hexane or water/n-heptane, and at a suitable temperature within the range from about 0–50° C. Such enzymatic treatment results in hydrolysis of one of the enantiomers, thus obtaining a mixture of either (3a) and (3) or a mixture of (4) and (4a). If the mixture of (3) and (3a) is obtained, then the mixture is separated in a well known manner to obtain compound (3). If the mixture of (4) and (4a) is obtained, then (4) is isolated and hydrolysed in a well known manner to obtain compound (3). The compound of formula (3) is then treated with an alkylating agent, such as an agent of formula Y—R$^5$ wherein Rs and Y are as defined above, e.g. chloroethylpyrrolidine, thereby obtaining a compound of formula (5). One way to carry out the alkylating step is described in Ray et al. J. Med. Chem. 19, p. 276–279 (1976).

Scheme 2

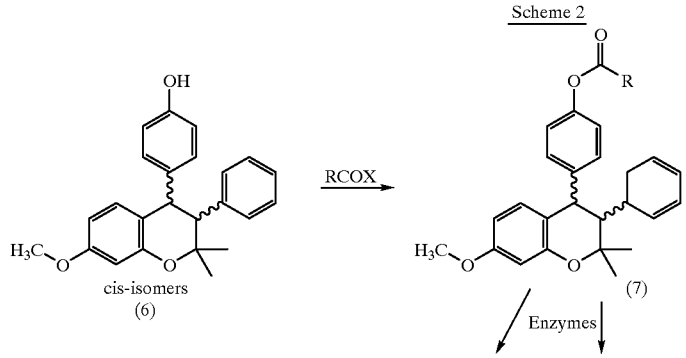

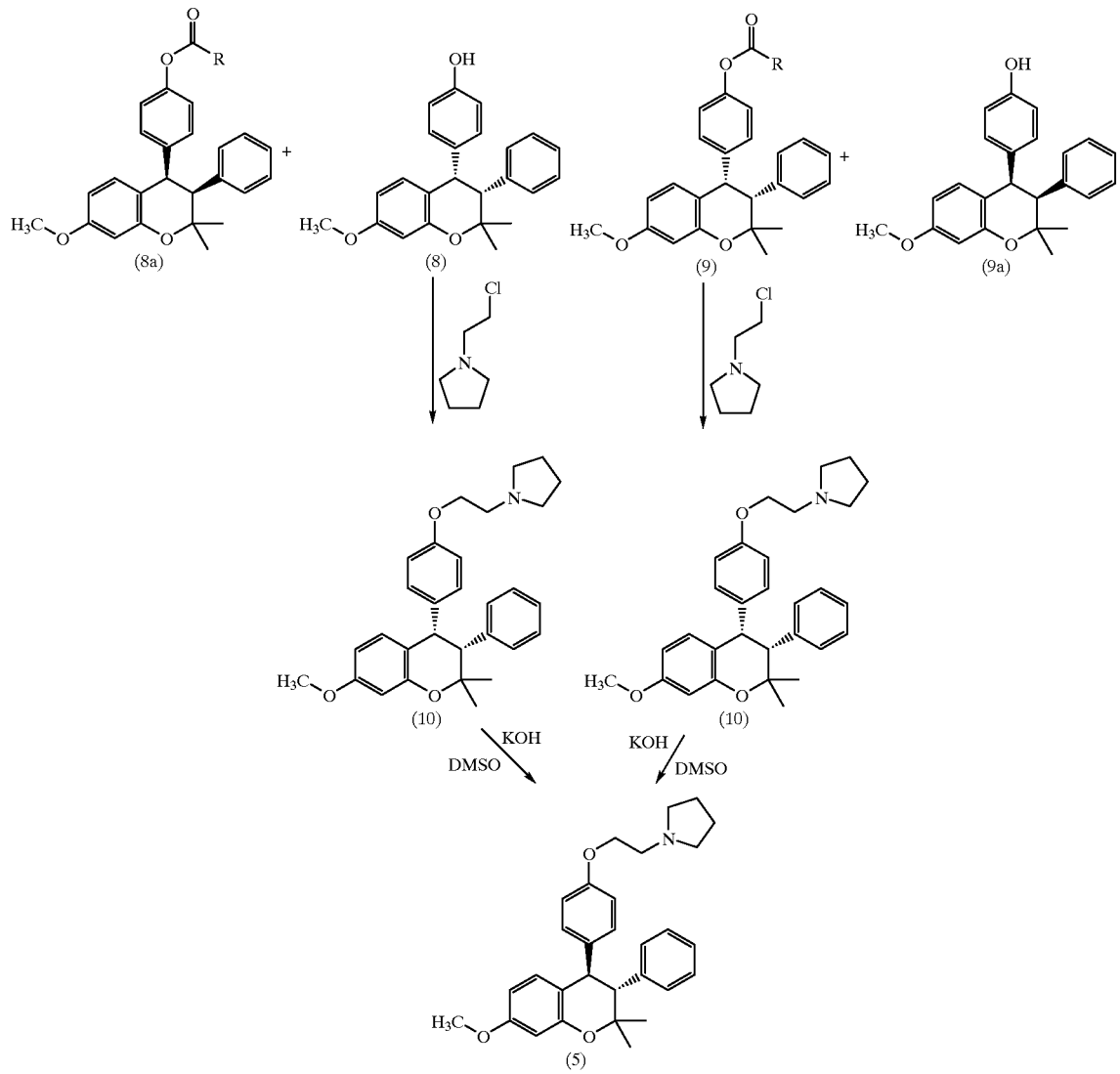

Cis-racemate of formula (6) is treated with an acylating agent, such as an agent of formula R—CO—X, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby obtaining the protected cis-racemate of formula (7). The cis-isomers of formula (6) are commercially available or may be prepared according to well defined procedures disclosed in the prior art starting from commercially available starting compounds. The cis-isomers of formula (7) are then treated with an enzyme having lipase activity, e.g. candida antartica lipase B, Lipozyme, Humicola, *Pseudomonas cepasia, Candida cylindracea*, Pig liver esterase and Pig pancreas lipase, in a suitable solvent, such as an organic solvent, e.g. n-hexane, n-heptane, acetonitril, methanol or ethanol, or an aqueous/organic solvent mixture, e.g. water/n-hexane or water/n-heptane, and at a suitable temperature within the range from about 0–50° C. Such enzymatic treatment results in hydrolysis of one of the enantiomers, thus obtaining a mixture of either (8a) and (8) or a mixture of (9) and (9a). If the mixture of (8) and (8a) is obtained, then the mixture is separated in a well known manner to obtain compound (8). If the mixture of (9) and (9a) is obtained, then (9) is isolated and hydrolysed in a well known manner to obtain compound (8). The compound of formula (8) is then treated with an alkylating agent, such as an agent of formula Y—$R^5$ wherein $R^5$ and Y are as defined above, e.g. chloroethylpyrrolidine, thereby obtaining a compound of formula (10). The compound (10) is then treated with a strong base in an aprotic solvent, e.g. potassium hydroxide in dimethylsulfoxide, thereby obtaining a compound of formula (5). One way to carry out the alkylating step is described in Ray et al. J. Med. Chem. 19, p. 276–279 (1976).

In scemes 1 and 2 above, the compounds of formulas (1), (2), (3), (3a), (4), (4a), (5), (6), (7), (8), (8a), (9), (9a) and (10) are shown for the purpose of illustrating the present process, and should by no means limit the invention in any aspect.

In a particularly preferred embodiment the (−)-3R,4R-trans-7-methoxy-2,2-dimethyl-3-phenyl-4-{4-[2-(pyrrolidin-1-yl)ethoxy]phenyl}chromane is isolated as the hydrogen fumarate salt.

In the above structural formulas and throughout the present specification, the following terms have the indicated meanings:

The $C_{1-12}$-alkyl, $C_{1-6}$-alkyl or $C_{1-4}$-alkyl groups specified above are intended to include those alkyl groups of the designated length in either a linear or branched or cyclic configuration. Examples of linear alkyl are methyl, ethyl, n-propyl, n-butyl, pentyl, n-amyl, hexyl, n-hexyl and the like. Examples of branched alkyl are isopropyl, sec-butyl, tert-butyl, 2-ethylbutyl, 2,3-dimethylbutyl, isopentyl, sec-amyl, and isohexyl. Examples of cyclic alkyl are $C_{3-6}$ cycloalkyl such as cyclopropyl, cyclobutyl, cyclopentyl and cyclohexyl.

The $C_{1-12}$-alkoxy, $C_{1-6}$-alkoxy or $C_{1-4}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$-alkyl, $C_{1-6}$-alkoxy, halogen, amino or aryl.

Herein, the term "5- or 6-membered heterocyclic group containing one or two hetero atom(s)" include groups wherein the heteroatom(s) preferably are selected among N, O, or S such as e.g., piperidine, pyrrolidine, N-methylpiperazine or morpholine.

"Halogen" includes chloro, fluoro, bromo and iodo.

As hydrolyzing agent in step c) is normally used a weak base such as e.g. aqueous ammonia, sodium carbonate, potassium carbonate or the like, or an enzyme having lipase activity.

As strong bases for the rearrangement may be used potassium hydroxide, sodium hydroxide, metal alkoxides, such as sodium methoxide, sodium ethoxide or potassium t-butoxide, sodium hydride, alkyllithiums such as n-butyllithium and sec-butyllithium; methal amides, such as sodium amide, magnesium diisopropylamide and lithium diisopropylamide or the like. The preferred strong bases are potassium hydroxide and potassium t-butoxide.

The treatment with the strong base is normally carried out by heating the mixture, preferably at 80–110° C.

The preferred aprotic solvents are dimethylsulfoxide (DMSO), dimethylformamide (DMF), N-methylpyrrolidone (NMP) and toluene or combinations thereof. The combination NMP and toluene is preferred. The combination toluene and DMSO is another preferred.

In the present context, the term "leaving group" (as used in connection with X and Y) is intended to comprise any suitable group within the definition of leaving groups as defined in Advanced Organic Chemistry, by J. March, "Reactions, Mechanisms and Structures", 4. Ed., page 205, and includes e.g. a halogen or an acid residue e.g. a group of formula —O—CO—$C_{1-12}$alkyl.

In the present context, the term "enzyme having lipase activity" is intended to mean any hydrolase or lipase as comprised in EC 3.11.1.3, and any modification thereof, which modification have retained the hydrolysing ability of the enzyme. The enzyme having lipase activity may be derived by means involving the use of a microorganism or by recombinant means.

Within the present invention, the compounds of formulas I, II, III, IIIa, IIIb, IV, IVa, V, VI, VIa, VIb, VII, VIIa, and VII may be prepared in the form of salts thereof e.g. pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained from the free base in a suitable solvent containing the appropriate acid, and the salt isolated by evaporating the solvent or otherwise separating the salt and solvent e.g. by crystallisation.

The starting compound for the process, e.i. the cis-racemate of formula (V) or the trans-racemate of formula (II) may be prepared according to known methods, such as those disclosed in Ray et al., *J Med Chem* 19 (1976), 276–279.

Further embodiments of the present process may be provided by any possible combination of any one of the above embodiments.

The process of the invention is described in greater detail in the following non-limitative examples.

EXAMPLE 1 trans-(+/−)-4-Hydroxyphenyl-7-methoxy-2,2-dimethyl-3-phenylchromane cis-(+/−)-4-Hydroxyphenyl-7-methoxy-2,2-dimethyl-3-phenylchromane (50 g) was refluxed in a mixture of toluene (500 ml), dimethylsulfoxide (100 ml) and potassium hydroxide (20 g) for 12 hours. The reflux was carried out with a condenser equipped with a water trap for removing water from the reaction mixture during the process. The reaction mixture was poured into diluted hydrochloric acid (500 ml 1M). The product was filtered off and dried.

Yield 48.6 g (97%), m.p.=267° C.

The identity of the product was verified by $^1$H-NMR.

EXAMPLE 2 cis-(+/−)-4-Acetoxyphenyl-7-methoxy-2,2-dimethyl-3-phenylchromane cis-(+/−)-4-Hydroxyphenyl-7-methoxy-2,2-dimethyl-3-phenylchromane (3.6 g) was dissolved in acetic anhydride (10.8 g). Triethylamine (1.45 g) was added and the mixture stirred at ambient temperature for 3 hours. The mixture was evaporated in vacuum. The residue was partitioned between water (100 ml) and ethyl acetate (200 ml). The organic phase was separated washed with 1M sodium hydroxide, brine and dried over sodium sulphate evaporated and the residue crystallised from a mixture of water (10 ml) and ethanol (30md).

Yield 3.6 g (89%). M.p.=121.5–123° C.

The identity of the product was verified by [1] H-NMR and Mass Spectroscopy.

EXAMPLE 3 cis-(+/−)-4-Hexanoyloxyphenyl-7-methoxy-2,2-dimethyl-3-phenylchromane cis-(+/−)-4-Hydroxyphenyl-7-methoxy-2,2-dimethyl-3-phenylchromane (7.2 g) was dissolved in tetrahydrofuran (20 ml). Triethylamine (8 ml) and hexanoyl chloride (5.4 g) was added and the mixture stirred at ambient temperature overnight. The mixture was poured into water and extracted with ethyl acetate (100ml). The organic phase was separated and washed with 10 % sodium bicarbonate solution and dried over sodium sulphate. The organic extract was evaporated to an heavy oil.

Yield 6 g (75%).

The identity of the product was verified by $^1$ H-NMR.

EXAMPLE 4 cis-(+/−)-4-Ethoxycarbonyloxyphenyl-7-methoxy-2,2-dimethyl-3-phenylchromane cis-(+/−)-4-Hydroxyphenyl-7-methoxy-2,2-dimethyl-3-phenylchromane (7.2 g) was dissolved in tetrahydrofuran (20 ml). Triethylamine (4.2 ml) and ethyl chloroformate (3.8 ml) was added and the mixture stirred at ambient temperature overnight. The mixture was poured into ice water and extracted with ethyl acetate (100 ml). The organic phase was separated and washed with brine and dried over sodium sulphate. The organic extract was evaporated and crystallised from ethanol.

Yield 7.2 g(96%). M.p.=112° C.

The identity of the product was verified by $^1$H-NMR.

EXAMPLE 5 trans-(+/−)-4-Acetoxyphenvl-7-methoxy-2,2-dimethyl-3-phenylchromane trans-(+/−)-4-Hydroxyphenyl-7-methoxy-2,2-dimethyl-3-phenylchromane (3.6 g) was dissolved in acetic anhydride (20 ml). Triethylamine (4 ml) was added and the mixture stirred at ambient temperature overnight. The mixture was evaporated in vacuum. The residue was stirred with water (100 ml). The solid was filtered off and recrystallised from ethanol water.

Yield 5.2 g (76%). M.p.=192° C.

The identity of the product was verified by $^1$H-NMR.

EXAMPLE 6 trans-(+/−)-4-Hexanoyloxyphenyl-7-methoxy-2,2-dimethyl-3-phenylchromane trans-(+/−)-4-Hydroxyphenyl-7-methoxy-2,2-dimethyl-3-phenylchromane (7.2 g) was dissolved in tetrahydrofuran (20 ml). Triethylamine (8 ml) and hexanoyl chloride (5.4 g) was added and the mixture stirred at ambient temperature overnight. The mixture was poured into water and extracted with ethyl acetate (100 ml). The organic phase was separated and washed with 10% sodium bicarbonate solution and dried over sodium sulphate. The organic extract was evaporated to an heavy oil and crystallised from light petroleum.

Yield 5.5g (69%).M.p.=95° C.

The identity of the product was verified by $^1$H-NMR.

EXAMPLE 7 trans-(+/−)-4-Ethoxycarbonyloxyphenyl-7-methoxy-2,2-dimethyl-3-phenylchromane trans-(+/−)-4-Hydroxyphenyl-7-methoxy-2,2-dimethyl-3-phenylchromane (7.2 g) was dissolved in tetrahydrofuran (30 ml). Triethylamine (4.2 ml) and ethyl chloroformate (3.8 ml) was added and the mixture stirred at ambient temperature overnight. The mixture was poured into ice water and extracted with ethyl acetate (100 ml). The organic phase was separated and washed with brine and dried over sodium sulphate. The organic extract was evaporated and crystallised from ethanol.

Yield 7.4 g(99%). M.p.=150° C.

The identity of the product was verified by $^1$H-NMR.

EXAMPLE 8 cis-3R,4S-7-Methoxy-3-phenyl 4-{4-[2-(pyrrolidin-1-yl)ethoxy]phenyl}chromane.

cis-3R,4S-4-(4-Hydroxyphenyl)-7-methoxy-3-phenylchromane synthesised in an enzymatic hydrolysis of cis-(+/−)-4-acetoxyphenyl-7-methoxy-2,2-dimethyl-3-phenylchromane (500 mg) in hexane was isolated from cis-3S,4R-4-(4-acetoxyphenyl)-7-methoxy-3-phenylchromane in the hydrolysis mixture by crystallisation at −18° C.

The product was dissolved in acetone (20 ml) and refluxed overnight with potassium carbonate and chloroethylpyrrolidine hydrochloride (300 mg). The reaction mixture was partitioned between water and toluene. The organic phase was separated, dried over potassium carbonate and evaporated to an oil.

The product was identified on HPCE as cis-3R,4S-7-methoxy-3-phenyl 4-{4-[2-(pyrrolidin-1-yl)ethoxy]phenyl}chromane which is the precursor to levormeloxifene.

EXAMPLE 9

(−)-trans-7-Methoxy-2,2-dimethyl-3-phenyl-4-{4-[2-(pyrrolidin-1-yl)ethoxy]phenvy}chromane hydrogenfumarate (−)-cis-7-Methoxy-2,2-dimethyl-3-phenyl-4-{4-[2-(pyrrolidin-1-yl)ethoxy]phenyl}chromane (−)-O,O'-ditoluoyltartrate (66.3 g) (or the basic compound: (−)-cis-7-Methoxy-2,2-dimethyl-3-phenyl-4-{4-[2-(pyrrolidin-1-yl)ethoxy]phenyl}chromane in an amount corresponding to the chiral (−)-O,O'-ditoluoyltartrate salt) was suspended in a mixture of toluene (330 ml), water (265 ml) and sodium carbonate (20.8 g). The mixture was stirred until all salts have dissolved. The aqueous phase was separated and extracted with another portion of toluene (65 ml). The combined organic phase was washed with water (3×130 ml). The organic phase was dried by removal of water in an azeotropic distillation. To the dry toluene solution was added dimethylsulfoxide (66 ml) and finely grinded potassium hydroxide (15.4 g). The mixture was heated to reflux while water was distilled from the mixture. The reflux was maintained for 6 hours. The reaction mixture was cooled down to room temperature, water (200 ml) was added and the mixture stirred until all the salt was dissolved. The aqueous phase was separated and extracted with another portion of toluene (135 ml). The organic phases were pooled washed with water (2×200 ml) and evaporated to an oil. The oil was dissolved in ethanol (135 ml) at 40° C. and mixed with a solution of fumaric acid (9.1 g) in ethanol (265 ml) at 40–60° C. The mixture was stirred for 2 hours at ambient temperature and then for 1 hour at 0° C. The crystals were filtered off and dried.

By Chiral HPLC the enantiomeric purity was determined to be better than 99.5% and the identity to be hydrogen fumarate salt of levormeloxifene, i.e. the minus enantiomer of the racemic compound Centchroman. Chiral HPLC system: Column: Chiradex 5 , 250×4 mm(Merck). Eluent: 70% methanol/buffer (0.25% triethylammonium acetate, pH=5.2).

Yield 43 g (85%), m.p. 220° C. with slight decomposition. The structure of the compound was verified by $^1$H-NMR and elemental analysis.

EXAMPLE 10

Cis-3R,4S-4-(4-Hydroxyphenyl)-7-methoxy-3-phenylchromane 500 mg cis-(+/−)-4-acetoxyphenyl-7-methoxy-2,2-dimethyl-3-phenylchromane dissolved in 200 ml n-hexane was added to 50 ml buffer/enzyme suspension consisting of 550 mg *Candida cylindracea* Lipase (EC3.1.1.3, 2.3 U/mg, Fluka) and 50 ml 50 mM fosphate buffer pH 7.0. The suspension was stirred with a magnet (450 rounds/minute) for 206 minuttes. The organic phase was dryed with magnesium sulphate. Chiral CE analysis showed that the conversion was app. 60% with an ee=69% for the title product.

Cis-3R,4S-4-(4-Hydroxyphenyl)-7-methoxy-3-phenylchromane was isolated from cis-3S,4R-4-(4-acetoxyphenyl)-7-methoxy-3-phenylchromane in the hydrolysis mixture by crystallisation at −18° C.

The CE system was: 5 mM sulfobuthylether-beta-cyclodextrin in 75 mM fosphate buffer, pH 2.5. The capillary was 83.5 cm long and with 50 μm internal diameter. The conditions were −20 kV/−35 μA, 30° C. and samples were injected for 3.0 seconds with 50 mBar. 10 μl samples were taken from the reaction mixture and dilluted in 300 μl acetonitrile plus 300 μl fosphate buffer.

What is claimed is:

1. A process for the preparation of (−)-3,4-trans-compounds of the formula I

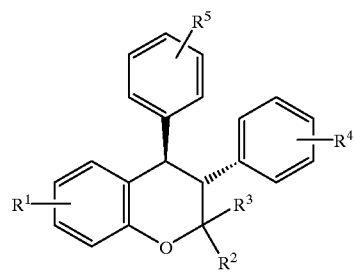

(I)

wherein $R^1$ and $R^4$ are individually hydrogen, $C_{1-6}$alkyl or $C_{1-6}$alkoxy, $R^5$ is —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6-membered heterocyclic group containing one or two heteroatom(s) which heterocyclic group is optionally substituted with $C_{1-6}$alkyl; and $R^2$ and $R^3$ are individually hydrogen or $C_{1-6}$alkyl; or a salt thereof, which comprises a) treating a cis-racemate of a compound of formula V

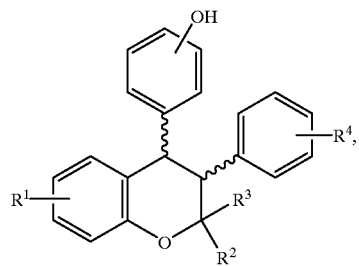

(V)

or a salt thereof, wherein $R^1$, $R^2$, $R^3$ and $R^4$ are as defined above with an agent of formula R—CO—X, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby providing a cis-racemate of a compound of formula VI

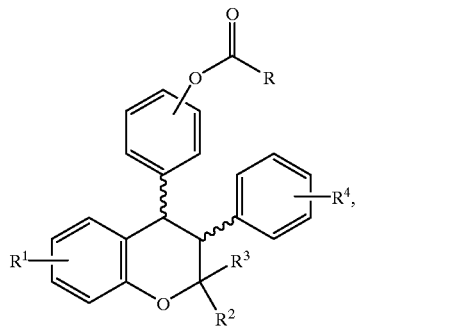

(VI)

or a salt thereof, wherein R, $R^1$, $R^2$, $R^3$ and $R^4$ are as defined above, b) treating said cis-racemate of formula VI with an enzyme having lipase activity, thereby providing a mixture comprising a compound of formula VIa

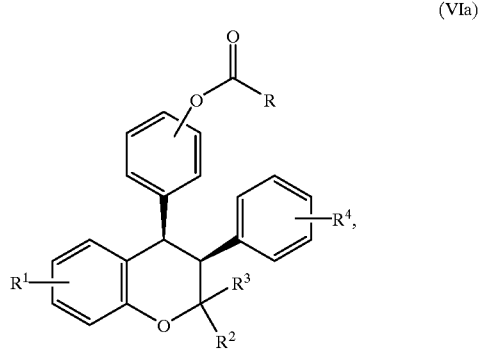

(VIa)

or a salt thereof, and a compound of formula VII

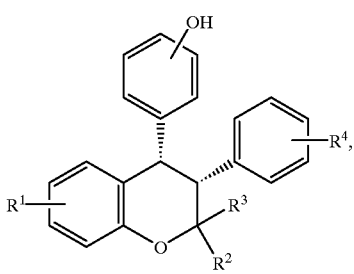

(VII)

or a salt thereof, or a mixture comprising a compound of formula VIb (VIb)

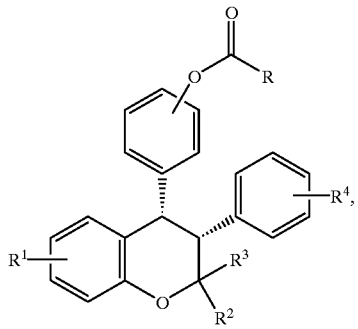

or a salt thereof, and a compound of formula VIIa (VIIa)

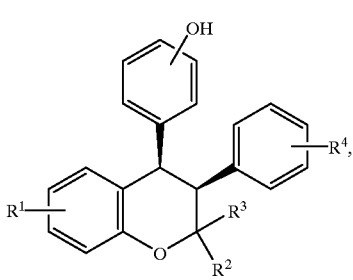

or a salt thereof, c) separating said mixture of compound VIa and VII or said mixture of compound VIb and VIIa, thereby obtaining a compound of formula VII or a compound of formula VIb, which compound VIb is then hydrolyzed to said compound of formula VII, d) treating said compound of formula VII or a salt thereof, with an agent of formula Y—$R^5$ wherein Y is leaving group, thereby providing a compound of formula VIII (VIII)

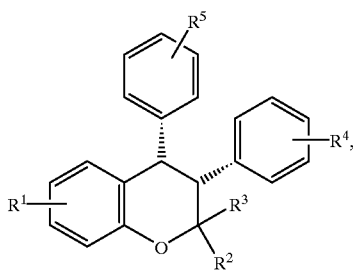

or a salt thereof, e) treating said compound of formula VIII or a salt thereof with a strong base in an aprotic solvent, thereby obtaining said compound of formula I or a salt thereof.

2. A preparation of (−)-3,4-trans-compounds of the formula I (I)

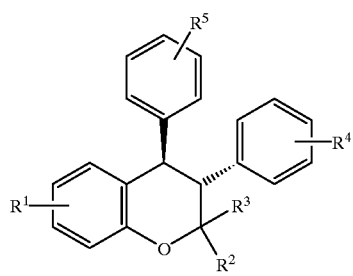

wherein $R^1$ and $R^4$ are individually hydrogen, $C_{1-6}$alkyl or $C_{1-6}$alkoxy, $R^5$ is —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6-membered heterocyclic group containing one or two heteroatom(s) which heterocyclic group is optionally substituted with $C_{1-6}$alkyl; and $R^2$ and $R^3$ are individually hydrogen or $C_{1-6}$alkyl; or a salt thereof, which comprises a) treating a trans-racemate of a compound of formula II (II)

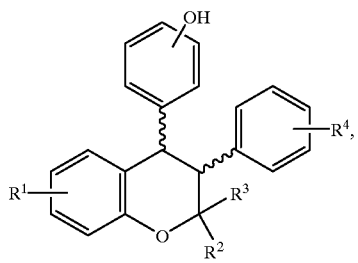

or a salt thereof, wherein $R^1$, $R^2$, $R^3$ and $R^4$ are as defined above with an agent of formula R—CO—X, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby providing a trans-racemate of a compound of formula III (III)

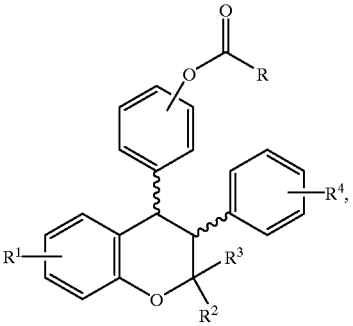

or a salt thereof, wherein $R^1$, $R^2$, $R^3$ and $R^4$ are as defined above, b) treating said trans-racemate of formula III with an enzyme having lipase activity, thereby providing a mixture comprising a compound of formula IIIa

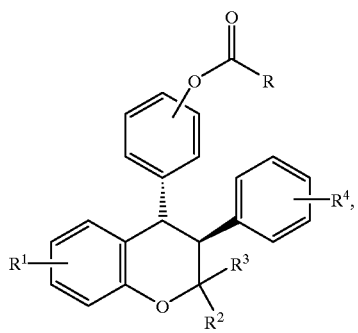

or a salt thereof, and a compound of formula IV

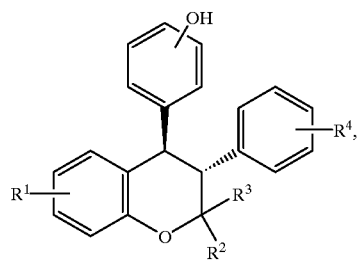

or a salt thereof;
or a mixture comprising a compound of formula IIIb

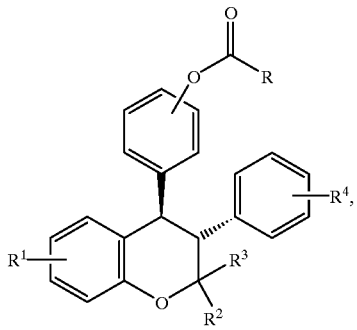

or a salt thereof, and a compound of formula IVa

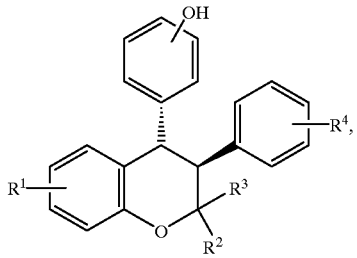

or a salt thereof;

c) separating said mixture of compound IIIa and IV or said mixture of compound IIIb and IVa, thereby obtaining a compound of formula IV or a compound of formula IIIb, which compound IIIb is then hydrolyzed to said compound of formula IV, d) treating said compound of formula IV with an agent of formula Y—$R^5$ wherein Y is a leaving group, thereby obtaining the compound of formula I or a salt thereof.

3. The process according to claim 1, wherein $R^1$ is $C_{1-6}$alkoxy, $R^2$ and $R^3$ are the same and are $C_{1-6}$alkyl, $R^4$ is hydrogen and $R^5$ is —O—$(CH_2)_n$—$NR^6R^7$ wherein n is 2 and $R^6$ and $R^7$ together with the N atom is a saturated or unsaturated 5- or 6-membered heterocyclic group containing one or two heteroatom(s) and optionally substituted with $C_{1-6}$alkyl.

4. The process according to claim 1 wherein $R^1$ is in the 7-position and $R^5$ is in the 4-position.

5. The process according to claim 1 wherein in said agent of formula R—CO—X, R is $C_{1-12}$alkyl or $C_{1-12}$alkoxy, and X is a halogen or a —O—CO—$C_{1-6}$alkyl.

6. The process according to claim 1 wherein said enzyme is a lipase.

7. The process according to claim 1 wherein in said agent of formula Y—$R^5$, Y is a halogen.

8. The process according to claim 1 wherein said strong base in an aprotic solvent is potassium hydroxide in dimethylsulfoxide and toluene, or potassium t-butoxide in N-methylpyrrolidine and toluene.

9. A process for the preparation of (3R,4S)-cis-compounds of the formula VII

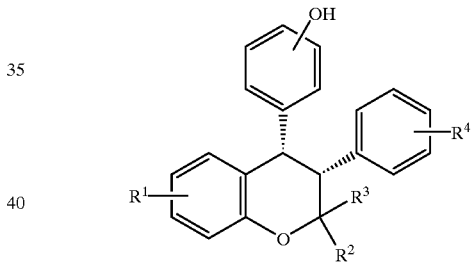

wherein $R^1$ and $R^4$ are individually hydrogen, $C_{1-6}$alkyl or $C_{1-6}$alkoxy, and $R^2$ and $R^3$ are individually hydrogen or $C_{1-6}$alkyl; or a salt thereof, which comprises a) treating a cis-racemate of a compound of formula V

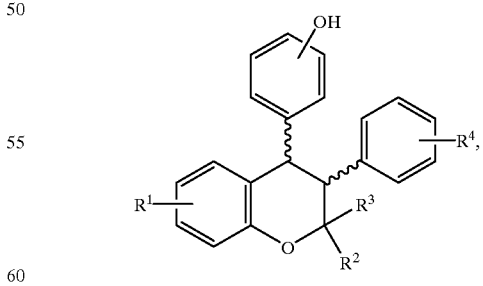

or a salt thereof, wherein $R^1$, $R^2$, $R^3$ and $R^4$ are as defined above with an agent of formula R—CO—X, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby providing a cis-racemate of a compound of formula VI (VI)

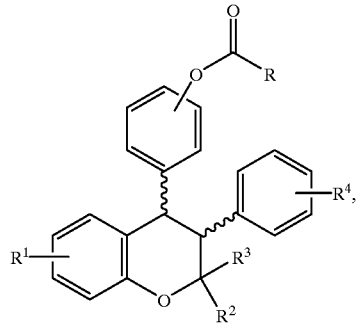

or a salt thereof, wherein R, R$^1$, R$^2$, R$^3$ and R$^4$ are as defined above, b) treating said cis-racemate of formula VI with an enzyme having lipase activity, thereby providing a mixture comprising a compound of formula VIa (VIa)

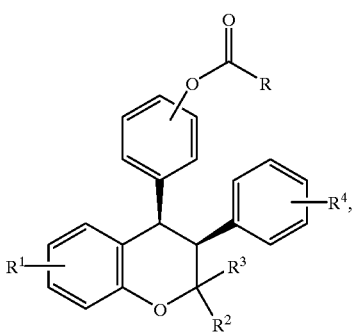

or a salt thereof, and a compound of formula VII (VII)

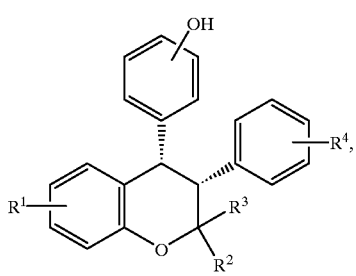

or a salt thereof;

or a mixture comprising a compound of formula VIb (VIb)

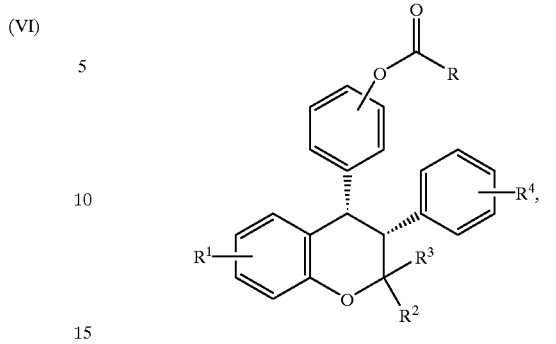

or a salt thereof, and a compound of formula VIIa (VIIa)

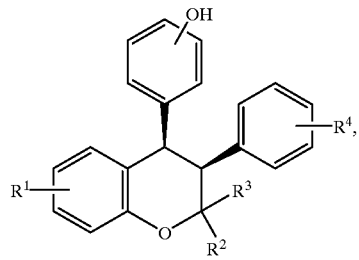

or a salt thereof, c) separating said mixture of compound VIa and VII or said mixture of compound VIb and VIIa, thereby obtaining a compound of formula VII or a compound of formula VIb, which compound VIb is then hydrolyzed to said compound of formula VII.

10. The process according to claim 9 further comprising the step of treating said compound of formula VII or a salt thereof, with an agent of formula Y—R$^5$ wherein Y is a leaving group and R$^5$ is —O—(CH$_2$)$_n$—NR$^6$R$^7$ wherein n is an integer in the range of 1 to 6 and R$^6$ and R$^7$ independently are C$_{1-6}$alkyl or R$^6$ and R$^7$ together with the N atom is a saturated or unsaturated 5- or 6-membered heterocyclic group containing one or two heteroatom(s) which heterocyclic group is optionally substituted with C$_{1-6}$alkyl, thereby providing a compound of formula VIII (VIII)

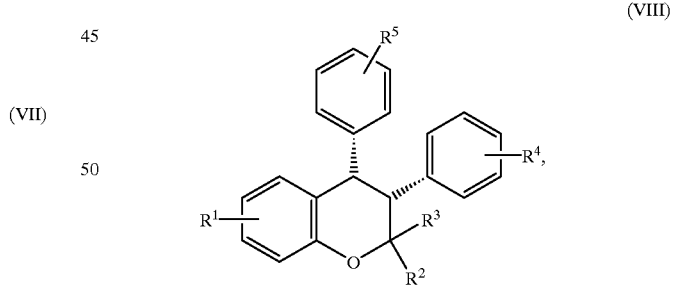

or a salt thereof.

11. The process according to claim 10 wherein in said agent of formula Y—R$^5$, Y is a halogen.

12. The process according to claim 10 wherein R$^5$ is pyrrolidinoethoxy.

13. The process according to claim 10 further comprising the step of treating said compound of formula VIII or a salt thereof with a strong base in an aprotic solvent, thereby obtaining said compound of formula I or a salt thereof.

14. The process according to claim 13 wherein said strong base in an aprotic solvent is potassium hydroxide in dimethylsulfoxide and toluene, or potassium t-butoxide in N-methylpyrrolidine and toluene.

15. The process according to claim 9 wherein said enzyme is a lipase.

16. A process for the preparation of (3R,4R)-trans-compounds of the formula IV

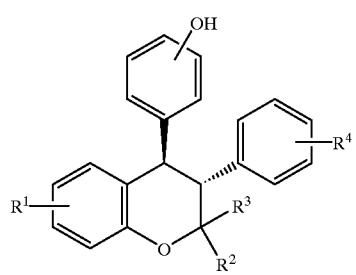

(IV)

wherein $R^1$ and $R^4$ are individually hydrogen, $C_{1-6}$alkyl or $C_{1-6}$alkoxy, and $R^2$ and $R^3$ are individually hydrogen or $C_{1-6}$alkyl; or a salt thereof, which comprises a) treating a trans-racemate of a compound of formula II

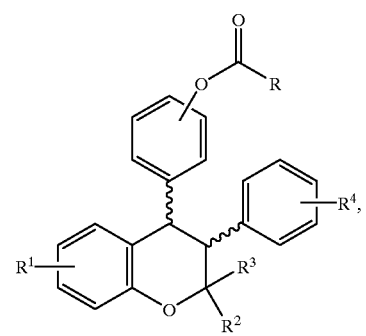

(II)

or a salt thereof, wherein $R^1$, $R^2$, $R^3$ and $R^4$ are as defined above with an agent of formula R—CO—X, wherein R is $C_{1-12}$alkyl, optionally substituted with $C_{1-6}$alkyl, $C_{1-6}$alkoxy, hetaryl or aryl or $C_{1-12}$alkoxy, optionally substituted with $C_{1-6}$alkyl, $C_{1-6}$alkoxy, hetaryl or aryl, and X is a leaving group, thereby providing a trans-racemate of a compound of formula III (III)

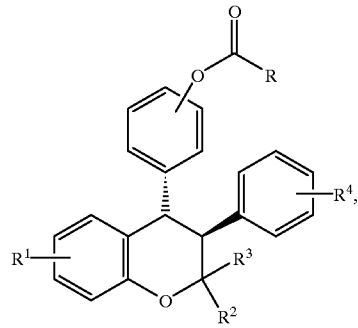

or a salt thereof, wherein $R^1$, $R^2$, $R^3$ and $R^4$ are as defined above, b) treating said trans-racemate of formula III with an enzyme having lipase activity, thereby providing a mixture comprising a compound of formula IIIa (IIIa)

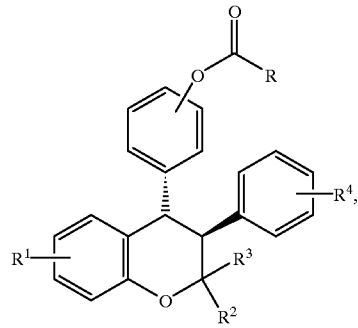

or a salt thereof, and a compound of formula IV (IV)

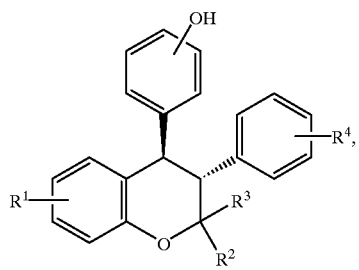

or a salt thereof;
or a mixture comprising a compound of formula IIIb (IIIb)

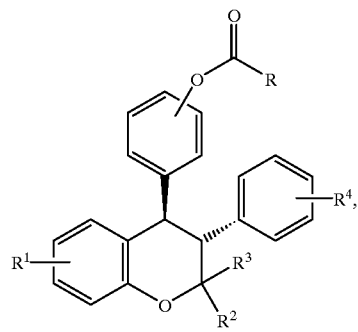

or a salt thereof, and a compound of formula IVa (IVa)

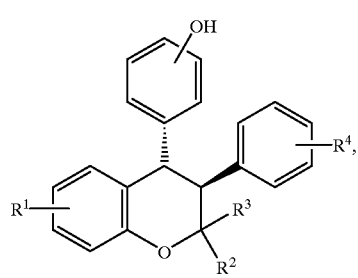

or a salt thereof, c) separating said mixture of compound IIIa and IV or said mixture of compound IIIb and IVa, thereby obtaining a compound of formula IV or a compound of formula IIIb, which compound IIIb is then hydrolyzed to said compound of formula IV, or a salt thereof.

17. The process according to claim 16 further comprising the step of treating said compound of formula IV with an agent of formula Y—$R^5$ wherein $R^5$ is —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6-membered heterocyclic group containing one or two heteroatom(s) which heterocyclic group is optionally substituted with $C_{1-6}$alkyl and Y is a leaving group, thereby obtaining the compound of formula I or a salt thereof.

18. The process according to claim 17 wherein in said agent of formula Y—$R^5$, Y is a halogen.

19. The process according to claim 17 wherein $R^5$ is pyrrolidinoethoxy.

20. The process according to claim 16, wherein $R^1$ is $C_{1-6}$alkoxy, $R^2$ and $R^3$ are the same and are $C_{1-6}$alkyl and $R^4$ is hydrogen.

\* \* \* \* \*